US009438580B2

(12) United States Patent
Kupper et al.

(10) Patent No.: US 9,438,580 B2
(45) Date of Patent: Sep. 6, 2016

(54) AUTHENTICATING ACCESS TO CONFIDENTIAL INFORMATION BY UNREGISTERED REQUESTOR

(71) Applicants: Aric Sean Kupper, Brooklyn, NY (US); Brenda Pomerance, New York, NY (US)

(72) Inventors: Aric Sean Kupper, Brooklyn, NY (US); Brenda Pomerance, New York, NY (US)

( * ) Notice: Subject to any disclaimer, the term of this patent is extended or adjusted under 35 U.S.C. 154(b) by 0 days.

(21) Appl. No.: 14/247,713

(22) Filed: Apr. 8, 2014

(65) Prior Publication Data
US 2015/0288668 A1    Oct. 8, 2015

(51) Int. Cl.
| | |
|---|---|
| *G06F 21/62* | (2013.01) |
| *H04L 29/06* | (2006.01) |
| *H04L 29/08* | (2006.01) |
| *G06F 19/00* | (2011.01) |
| *H04W 4/22* | (2009.01) |

(52) U.S. Cl.
CPC ............ *H04L 63/08* (2013.01); *G06F 19/322* (2013.01); *G06F 21/6245* (2013.01); *H04L 67/10* (2013.01); *H04L 67/306* (2013.01); *H04W 4/22* (2013.01)

(58) Field of Classification Search
CPC ........ H04L 63/08; H04L 67/10; H04W 4/22; H04W 67/306; G06F 19/32; G06F 21/6245
USPC .......................................................... 726/4
See application file for complete search history.

(56) References Cited

U.S. PATENT DOCUMENTS

| | | | |
|---|---|---|---|
| 6,874,085 | B1 | 3/2005 | Koo |
| 7,162,641 | B1 * | 1/2007 | Chaudhari et al. ........... 713/186 |
| 7,905,417 | B2 | 3/2011 | Leiper |
| 8,537,002 | B2 | 9/2013 | Caplan |
| 2004/0229597 | A1 * | 11/2004 | Patel ............................. 455/411 |
| 2005/0055583 | A1 * | 3/2005 | Tanaka et al. ................ 713/202 |
| 2008/0126417 | A1 | 5/2008 | Mazurik |
| 2011/0173684 | A1 * | 7/2011 | Hurry et al. ...................... 726/6 |
| 2011/0221568 | A1 * | 9/2011 | Giobbi ......................... 340/5.82 |
| 2012/0137353 | A1 * | 5/2012 | Smales ............................. 726/7 |
| 2012/0209773 | A1 * | 8/2012 | Ranganathan ................. 705/44 |
| 2014/0033286 | A1 * | 1/2014 | Zhang ............................... 726/7 |
| 2014/0164254 | A1 * | 6/2014 | Dimmick ........................ 705/71 |

FOREIGN PATENT DOCUMENTS

| | | | | |
|---|---|---|---|---|
| GB | WO2013108018 | * | 7/2013 | ............. H04L 29/08 |
| WO | 2013020185 A1 | | 2/2013 | |

OTHER PUBLICATIONS

About ICE Blue Button, www.icebluebutton.com/about.html, Jan. 5, 2014.
ICEBlueButton home page, www.icebluebutton.com, Jan. 5, 2014.
Your Health Records: About Blue Button, www.healthit.gov/patients-families/blue-button/about-blue-button, Jan. 5, 2014.

* cited by examiner

*Primary Examiner* — Harunur Rashid
*Assistant Examiner* — Sakinah Taylor
(74) *Attorney, Agent, or Firm* — Brenda Pomerance

(57) ABSTRACT

An unregistered requestor requests access to confidential information of an individual stored at a computer. In one embodiment, the requestor is authenticated by the computer using at least two authentication tests. When the requestor is authenticated, the computer determines access permission for the requestor based on information provided from the requestor, and provides, to the requestor, access to the confidential information of the individual based on the access permission. In another embodiment, the computer presents a series of challenges to the requestor, and if any of the challenges is passed, access is granted.

18 Claims, 11 Drawing Sheets

|   | Individual (Primary) Access Privilege to: | Individual Name/Contact Info 111 | Individual Non-Medical Info 112 | Individual Medical Info 121 |
|---|---|---|---|---|
| R1 | Individual (Primary) (self) | read/write | read/write | read/write |
| R2 | Linked Primary | read | read | read if permitted |
| R3 | Secondary (Individual's Primary Account is the Master Account) | read/write | read/write | read/write |
| R4 | Linked Secondary (Individual's Primary Account is not the Master Account) | read write if permitted | read write if permitted | read write if permitted |

Fig. 2

|  | REGISTERED PROFILE Individual Information Access | | | AUTHENTICATED PROFILE Individual Information Access | | |
|---|---|---|---|---|---|---|
|  | Name/Contact 111 | Non-Medical 112 | Medical 121 | Name/Contact 111 | Non-Medical 112 | Medical 121 |
| PROFILE 1 Physician | read no write | read no write | read depends | read no write | read no write | read append |
| PROFILE 2A Non-physician/ Non-nurse HCP* | read no write | read no write | read append | not applicable | | |
| PROFILE 2B Licensed training physician | read no write | read no write | read append | read no write | read no write | read append |
| PROFILE 2C Unlicensed training physician | read no write | read no write | read append | read no write | read no write | read append |
| PROFILE 3 Nurse | read no write | read no write | read depends | not applicable | | |
| PROFILE 4 Medical first responder** | read no write | read no write | read no write | read no write | read no write | read no write |
| PROFILE 5 Non-medical first responder*** | read no write | read no write | no read no write | read no write | read no write | no read no write |
| PROFILE 6 Layperson | not applicable | | | read no write | no read no write | no read no write |
| PROFILE 7 Entity | read no write | no read no write | no read no write | not applicable | | |

\* E.g., physician's assistance, nurse practitioner
\*\* E.g., emergency medical technician (EMT), paramedic
\*\*\* E.g., police, firefighter, National Guard

Fig. 3A

|  | PROFILE AUTHENTICATION: WEIGHTING OF AUTHENTICATION ELEMENTS ||||||
|  | PRO-1-Approval 190 | ID-trusted-db 191 | Credit-card 192 | Indiv-approval 193 | Mobile-location 194 |
| --- | --- | --- | --- | --- | --- |
| PROFILE 1 | 0 | .40 | .20 | .20 | .20 |
| PROFILE 1 Approving | 0 | .50 | .25 | 0 | .25 |
| PROFILE 2A | .30 | .20 | .20 | .20 | .10 |
| PROFILE 2B | .40 | .20 | .20 | .20 | 0 |
| PROFILE 2C | .60 | 0 | .20 | .20 | 0 |
| PROFILE 3 | not applicable |||||
| PROFILE 4 | 0 | .40 | .35 | .15 | .10 |
| PROFILE 5 | 0 | .40 | .30 | .20 | .10 |
| PROFILE 6 | 0 | 0 | .50 | 0 | .50 |
| PROFILE 7 | not applicable |||||

Fig. 3B

| | Scoring of Authentication Elements |
|---|---|
| PRO-1-approval<br><br>190 | 5 pre-approved, or approved from trusted mobile, or approved with biometric<br>4 approved, other<br>4 unapproved due to tech difficulties & requestor approved in past 30 days<br>3 unapproved due to tech difficulties & requestor has default per-case PRO-1A<br>2 unapproved due to tech difficulties<br>0 approval explicitly denied |
| ID-trusted-db<br><br>191 | 5 unambiguous name in two trusted databases<br>4 unapproved due to tech difficulties & requestor approved in past 30 days<br>4 unambiguous name in one trusted database<br>4 ambiguous name in two trusted databases<br>3 ambiguous name in one trusted database<br>2 requestor name not found due to tech difficulties<br>0 not found in any trusted database & no tech difficulties |
| Credit-card<br><br>192 | 5 transaction approved<br>4 xtn unapproved due to tech difficulties & requestor approved in past 30 days<br>3 transaction unapproved due to tech difficulties<br>0 transaction denied |
| Indiv-approval<br><br>193 | 5 individual's consent code provided<br>4 info for one witness information provided<br>3 no consent code/witness provided & requestor approved in past 30 days<br>0 no consent code/witness provided |
| Mobile-location<br><br>194 | 5 registered mobile no. & location via cell triangulation or GPS<br>4 registered mobile no. & location via IP address<br>4 non-mobile & location via IP address<br>4 unregistered mobile no. & location via cell triangulation or GPS<br>3 registered mobile without location information<br>3 unregistered mobile no<br>2 non-mobile without IP address |

Fig. 3C

PIN 400

Honorific 410
Name 401
Emg_Contact 402
Emg_Contact_phone 403
Emg_Contact_email 404
Access_history 405

PIN 400

<< Password 406 >>
<< Security question 407 >>
<< Consent code 408 >>
Secondary 413
Birthdate 414
Age 416
Gender 418
Height 420
Weight 422
Face_photo 424
Identifying_char_text 426
Identifying_char_image 428
Residence_address 430
Residence_entity 431
Residence_phone 432
[Transfer_note 433]
Mobile_phone 434
Occupation 440
Employer 442
Employer_contact 443
Employment_address 444
Employment_phone 446
Spouse_Name 452
Dependant_Name 454
Dependant_Relation 456
Pet_Type 460
Religion 470
Legal_Power_Type 480
Legal_Power_Name 482
Legal_Power_Relation 484
Legal_Power_Phone 486
Legal_Power_Email 488
Legal_Power_Notif 490
Legal_Power_image 492

Emg_Contact_Name 500
Emg_Contact_Relation 502
Emg_Contact_Phone 504
Emg_Contact_Email 506
Emg_Contact_Notif 508
Insurance_Med_1 510
Insurance_Med_2 512
Insurance_Dental 514
Insurance_Vision 516
Insurance_Prescrip 518
Insurance_Other 520
Payment_source 530
Payment_method 532
<< Payment_acct 534 >>
<< Payment_code 536 >>
Linked_PIN_1 540
Secondary_PIN_1 550
Notification_Prefs 560
Access_history 570

PIN 400

Blood_type 605
Allergies 610
Current_Med_condition_1 620
Current_Med_condition_2 622
Past_Medical_condition_1 624
Past_Medical_condition_2 626
Past_Surgery_1 628
Past_Surgery_2 630
Special_requirements 640
Family_history 645
Medication_1 650
Medication_2 652
Medication_Admin_Record 654
Alcohol_history 660
Tobacco_history 670
Recreational_drug_history 680
Advance_directive_txt 690
Advance_directive_image 692
Immunization_history 700
Travel_history 710
Other_social 720
PCP 730
Dentist 732
Optometrist 734
Doctor_specialist_1 736
Doctor_specialist_2 738
Pharmacy 740
Lab_result_1 750
Lab_result_2 752
Xray_1 754
Xray_2 756
Other_image 758
Electrocardiogram 760
Notification_Prefs 770
Access_history 780

PRO_ID 800

Password 810
Security_question_1 812
Security_question_2 814
PRO_Type 815
Entity_affiliation 817
Face_photo 820
Biometric 822
Honorific 828
Name 830
Medical_speciality 832
[Default_PRO 837]
[PreapprovedBy_PRO 839]
Mobile_phone 840
Personal_email 842
Entity_phone 843
Entity_sponsor 844
Occupation 845
Employer 850
Employment_address 852
Employment_phone 854
Employment_email 856
Accepted_insurance 860
Residence_address 865
Residence_phone 870
Medical_license_state 875
Medical_license_number 877
National_Provider_Index 879
Credit_card_1 885
Credit_card_2 890
Payment 895
Notification_Prefs 897
Access_history 899

PRO_unreg 900

One-time_code 905
One-time_password 907
One-time_duration 909
PRO_Type 915
Biometric 920
Honorific 922
Name 930
Medical_speciality 932
Mobile_phone 940
Personal_email 942
Occupation 945
Employer 950
Employment_address 952
Employment_phone 954
Employment_email 956
Accepted_insurance 960
Residence_address 965
Residence_phone 970
Medical_license_state 975
Medical_license_no 977
Natl_Provider_Index 979
Credit_card_1 985
Credit_card_2 990
Payment 995
Notification_Prefs 997
Access_history 999

Entity_ID 2000

Password 2005
Security_question 2010
Entity_name 2020
Entity_address 2022
Entity_phone 2024
Entity_IP_address 2026
Entity_TaxID 2028
Admin_Name_1 2030
Admin_Email_1 2032
Admin_Username_1 2034
Admin_Password_1 2036
Admin_Security_Q_1 2038
Admin_Name_2 2040
Admin_Email_2 2042
Admin_Username_2 2044
Admin_Password_2 2046
Admin_Security_Q_2 2048
Accepted_Insurance 2050
Individual_account_1 2060
Individual_account_2 2062
Individual_1_resident 2061
Individual_2_resident 2063
PRO_account_1 2070
PRO_account_2 2072
Payment_max 2080
Invoice_type 2090
Invoice_recipient_name 2091
Invoice_recipient_email 2092
Invoice_recipient_phone 2093
Invoice_recipient_addr 2094
Alt_invoice_recip_name 2095
Alt_invoice_recip_email 2096
Alt_invoice_recip_phone 2097
Alt_invoice_recip_addr 2098

AUTHENTICATING ACCESS TO CONFIDENTIAL INFORMATION BY UNREGISTERED REQUESTOR

BACKGROUND OF THE INVENTION

The present invention relates to a computer system that enables an unregistered party to obtain access to another party's stored confidential information, and more particularly, is directed to a computer system that authenticates an unregistered party to grant access to another party's stored confidential information.

As used herein and in the claims, confidential information means information associated with an individual that cannot be determined merely by looking at the individual. As used herein and in the claims, the terms "confidential information" and "personal information" are interchangeable.

A patient is sometimes brought to a hospital emergency room in an unconscious condition. Emergency room doctors do the best they can, but in many cases could do better if they had the medical history of the patient prior to commencing treatment. After treatment, if the patient is still unconscious and cannot be identified, Medicare usually pays for the unidentified patient to be in the hospital for a month, then the patient is transferred to nursing care. Meanwhile, the family and friends of the unidentified or misidentified patient have no idea what happened.

Even if patients are conscious and competent to answer questions appropriately, they may not know what medications they are receiving, and their answers can be vague. For instance, one of the inventors asked a patient for the name of his primary care physician, and was told, "He's a small Indian man." This response was inadequate, although it was the best that the patient could do.

Moreover, the emergency room is a hectic place, and documents can easily be misplaced, particularly if the documents are being sent from one bureaucracy, such as a nursing home, to another bureaucracy, the hospital emergency room.

Accordingly, there is a need for emergency room doctors to have a better way of obtaining information about patients.

The U.S. government is promoting a "blue button", www.healthit.gov/patients-families/blue-button/about-blue-button, to enable patients to download their own health records to their own computer.

ICEBlueButton, www.icebluebutton.com, allows a user to create an ICE (In Case of Emergency) record on their smartphone. When a user downloads the application ("app") and launches it for the first time, the app asks the user to create an ICE record by tapping Add New Profile. The app presents a list of details to include:
  Personal Details
  Emergency Contacts
  An Authorized Representative
  Primary Physician
  Insurance Details
  Allergies
  Immunizations
  Medical Conditions
  Implanted Devices
A picture can be added to the profile, allowing would-be rescuers to ensure that the ICE record they are viewing matches the person in need of help.

The ICEBlueButton record data can also be auto-filled by extraction of Blue Button+ C-CDA data pushed to the Blue Button+enabled ICEBlueButton app by MU-2 or Blue Button+ compliant electronic medical records (EMRs). When more than one record is used to auto-fill the ICE record, the app aggregates data from the important clinical fields including medical conditions, medications and allergies.

The user then taps the Publish Profile button to send the newly created ICE record to a secure ICEBlueButton server. A quick response (QR) generated code (a two-dimensional black and white barcode that can be read by an imaging device) is stored within the phone's image gallery. The QR code can then be printed on stickers that can be applied to bike helmets, skateboards or backpacks; or on magnets that can be placed on a refrigerator. This QR-code can then be used as the phone's lock screen so that when the paramedic checks the phone of a patient in distress, they will scan the code and get a detailed history. In addition, when scanned, the app can send an email alert to emergency contacts, letting them know the name of the person whose code was scanned, and when and where (map location) the app was scanned.

A problem with ICEBlueButton is that anyone can scan the QR-code and get access to the patient's confidential medical information. Another problem is that the identity of the person obtaining the confidential medical information is unknown. This creates serious privacy concerns.

WO 2103020185, "Emergency contact device", is similar to ICEBlueButton, in that anyone can scan the QR-code for a patient and get access to the patient's confidential information.

U.S. Patent Application Publication 2008/0126417, "Systems and methods for emergency services, medical and community response to critical incidents", discloses checking the security level for a registered requestor of a patient's confidential information. However, if a requestor is unregistered, they cannot access the patient's information.

U.S. Pat. No. 6,874,085, "Medical records data security system", partitions a medical record into personal and medical portions. Access requires knowing the appropriate encryption key. If a patient arrives in the emergency room in an unconscious or confused condition, their stored information is thus unavailable.

U.S. Pat. No. 7,905,417, "Blinded electronic medical records", stores patient identification data and medical data in separate databases. Consolidators are permitted to transfer blinded (anonymous) medical data. This is not helpful for learning about an individual patient.

The Dossia Health Manager™, www.dossia.com, enables users to store and securely access their health information. However, access requires knowing the patient's user name and password.

None of the prior art known to the inventors properly balances the confidentiality of a patient's stored medical information with the urgent need to know of emergency personnel unregistered with the medical storage system.

SUMMARY OF THE INVENTION

In accordance with an aspect of this invention, there is provided a method for providing access to confidential information of an individual stored at a computer. At the computer, a request for the confidential information is received from a requestor. When the requestor is determined to be unregistered by the computer, the computer determines whether the requestor should be authenticated based on at least two authentication tests. When the requestor is authenticated, the computer determines access permission for the requestor based on information provided from the requestor, and provides, to the requestor, access to the confidential information of the individual based on the access permission.

In accordance with another aspect of this invention, there is provided a method for providing access, to an unregistered requestor, to personal information of a registered individual. A computer receives a personal identification number associated with the registered individual and a name of the unregistered requestor. The computer provides, to the unregistered requestor, a first challenge. When the unregistered requestor does not pass the first challenge, the computer provides, to the unregistered requestor, a second challenge. When the unregistered requestor does not pass the second challenge, the computer provides, to the unregistered requestor, a third challenge. When the unregistered requestor passes one of the first, second and third challenges, the computer provides, to the unregistered requestor, access to the personal information of the registered individual. When the unregistered requestor passes none of the first, second and third challenges, the computer denies, to the unregistered requestor, access to the personal information of the registered individual.

It is not intended that the invention be summarized here in its entirety. Rather, further features, aspects and advantages of the invention are set forth in or are apparent from the following description and drawings.

BRIEF DESCRIPTION OF THE DRAWINGS

FIGS. 2 and 3A-3C are tables referred to in discussing access permission;

FIGS. 4A, 4B, 5, 6A, 6B, 7 are charts showing data records used in the present invention;

DETAILED DESCRIPTION

A computer system stores an individual's name/contact data, non-medical data and medical data. When the individual's personal identification number (PIN) is provided to the computer system by a person previously registered with the system, access is provided immediately in accordance with the access permission in the requestor's registered profile. If the requestor is unregistered, then the system goes through a multi-step authentication procedure prior to providing access to the individual's information, with the amount of access depending on the credentials of the authenticated requestor and a scoring procedure. Thus, it is extremely difficult for persons lacking a need-to-know and proper credentials to obtain access to the individual's confidential information, which preserves the individual's privacy while enabling legitimate inquirers to gain access to the individual's confidential information.

Figure 1:
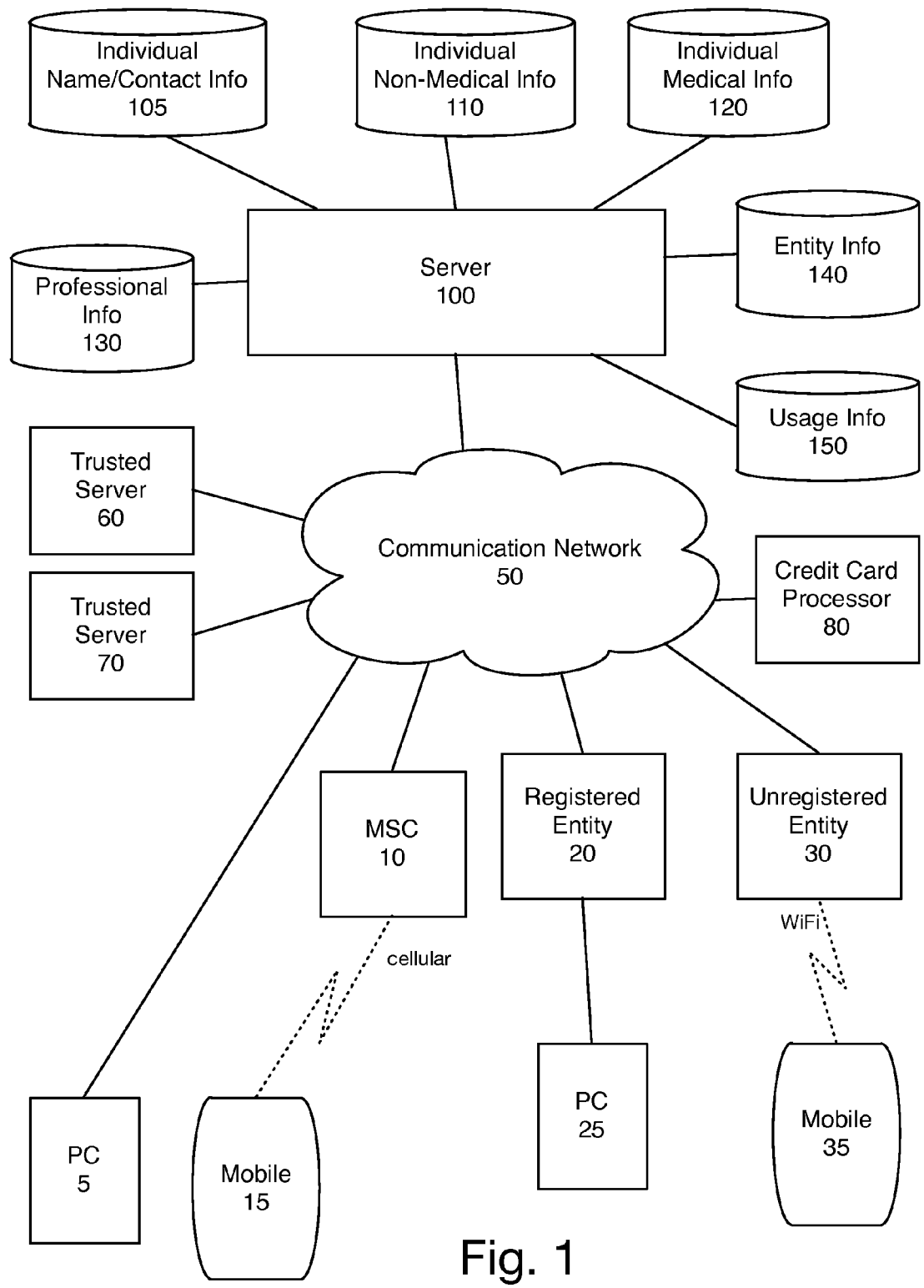
FIG. 1 is a block diagram showing the hardware and communications environment in which the present invention operates.

FIG. 1 is a block diagram showing the hardware and communications environment in which the present invention operates.

PC 5 is a general purpose personal computer coupled to communication network 50, such as the Internet, via a suitable wireline connection, such as a fiber optic line or CATV cable. PC 5 runs an operating system and a web browser program for interacting with websites. Mobile 15 is a general purpose computer capable of wireless communication with mobile switching center (MSC) 10 that, in turn, communicates with network 50. Mobile 15 may be a smartphone, a personal digital assistant, a portable computer or other suitable device. Mobile 15 runs an operating system and a web browser program.

Registered entity 20 represents a general purpose computer associated with an organization, such as a hospital or corporation, that communicates with network 50. Registered entity 20 runs an operating system, and provides communication infrastructure for its users, represented by PC 25. PC 25 is a general purpose computer running an operating system and web browser software. Registered entity 20 is responsible for paying for certain parties to use the medical information system described herein. Registered entity 20 may also provide wireless communication to its users.

Unregistered entity 30 represents a general purpose computer and communications infrastructure open to the public. For instance, unregistered entity 30 may be a coffee shop that provides WiFi access to its customers. Mobile 35 is a general purpose computer capable of wireless communication with unregistered entity 30. Mobile 35 may be a smartphone, a personal digital assistant, a portable computer or other suitable device. Mobile 35 runs an operating system and a web browser program. Unregistered entity 30 may also provide wireline communication to its users, such as a so-called Internet cafe with personal computers available for rent.

Although only one instance of each of PC 5, MSC 10, mobile 15, registered entity 20, PC 25, unregistered entity 30 and mobile 35 is shown, it will be understood that, in practice, there may be many instances of each of these.

Communication network 50 is a digital communication network, such as the Internet, that operates to send packets of data from one point to another via store-and-forward routing technology.

Trusted servers 60, 70 are each general purpose computers having generally reliable (trusted) identification information, and not necessarily specially adapted for use in the present invention. Servers 60, 70 accept queries and return responses. For instance, a government-operated server that enables look-up of licensed New York attorneys is at iapps.courts.state.ny.us/attorney/AttorneySearch. A government-operated server that enables look-up of registered patent attorneys and agents is at oedci.uspto.gov/OEDCI/. As another example, a government-operated server for verifying a National Provider Index (NPI) number for a doctor is at npiregistry.cms.hhs gov/NPPESRegistry/NPIRegistryHome.do. The New York State operated server that enables look-up of medical licenses is at www.health.ny.gov/professionals/doctors/conduct/license_lookup.htm. A national registry of licensed emergency medical technicians is at www.nremt.org; each state has their own registry of licensed medically-qualified first responders. For instance, the California registry of licensed medically-qualified first responders is at www.centralregistry.ca.gov. There are instances of trusted servers 60, 70 for physician assistants and nurse practitioners.

As another example, states have differing requirements to be a certified non-medical first responder, such as a police officer or firefighter. Presently, one wishing to verify that someone is a police officer typically calls the precinct, provides the name and badge of the alleged officer, and is told by the desk staff whether the alleged officer is a genuine officer. A police department computer operates as a trusted server when it accepts queries via network 50, and responds to verify or not verify a person as an officer.

Credit card processor 80 is a general purpose computer operative to enter an amount to be charged to the credit card network (not shown), and to confirm whether or not the charge was successfully processed.

A medical information system includes server 100 and databases 105, 110, 120, 130, 140. Server 100 is a general purpose computer or system of computers configured to operate in accordance with the present invention, including memory, database storage, communication facilities, an operating system and a custom program. The database storage can include one or many suitable magnetic, magneto-optical, optical or other disk drives and/or solid state memories for permanent storage. Preferably, a data record is distributed across several storage locations so that even if someone obtains unauthorized access, the full data record is difficult to obtain.

An account belongs to an individual, a health care professional or an entity.

An individual account is identified by a personal identification number (PIN) that serves, in this embodiment, as a username. In other embodiments, a username is uniquely associated with a PIN, for the convenience of the individual account owner; a PIN may be difficult to remember, but a username is usually mnemonic. An individual account stores the individual's name/emergency contact information, the individual's other non-medical information and the individual's medical information.

An individual account can be either a primary account or a secondary account. A primary account stores an individual's own information. A secondary account stores information for a dependent, such as a child, a disabled person or an elderly person. To link two primary accounts, such as a husband and wife, both parties must agree, and they can individually specify what the other party may access, e.g., a wife may not want to share her medical information with her husband. Each secondary account is linked to one primary account, designated as the master primary account; initially the master primary account is the one used for creating the secondary account, but this can be changed upon agreement of two primary account holders. A secondary account may be linked to additional primary accounts that are not the master primar account. To link a primary account and a secondary account, the master primary account holder and the other primary account holder must consent. An individual account can also be linked to an entity account (discussed below), for payment and/or updating permission.

FIG. 2 is a table showing access permission among individual accounts. Assume that Jane is an individual account holder, is linked to the primary account of her ex-spouse Henry, and is the master primary account for the secondary account of her minor son Philip. Assume that the ex-spouse Henry is the master primary account for the secondary account of her daughter Brooke, and that Jane's individual account is linked to Brooke's secondary account. As shown in row R1, Jane has full read and write permission for her own individual account, and, as shown in row R3, Jane has full read and write permission for Philip's secondary account. As shown in row R2, Jane can read Henry's non-medical information, but Henry has not yet agreed to let Jane view his medical information. As shown in row R4, Jane can read Brooke's information, but Henry has not yet agreed to let Jane write to Brooke's information. It will be appreciated that other combinations of linked and secondary accounts are possible, as needed to represent an individual's situation.

A professional account stores information for a registered health care provider or first-responder, to expedite processing during an access request. A professional account is identified by a professional identification (PRO_ID), similar to a username. Medical information is not stored in a professional account. A professional account can be linked to an individual account, to give the professional the ability to view and possibly update the medical information for the individual, which is useful for assisted living residences and skilled nursing facilities, and for individuals having medical issues that are best described by a professional. A professional account can be linked to an entity account, for payment. As explained below, a professional account may be linked to another professional account when there is a supervisor/trainee relationship between the professionals.

FIG. 3A is a table showing access permission for different types of professional accounts. A profile is a professional account having defined access permission for individual accounts. For this example, nine profiles PROFILES 1, 2A, 2B, 2C, 3, 4, 5, 6, 7 have been defined. In other embodiments, a greater or smaller number of profiles may be defined, with differing characteristics from those shown. In this embodiment, the information for which access permission is determined includes Individual-Name/Contact information 111 stored in database 105 (see FIG. 4A), Individual-Non-Medical information 112 stored in database 110 (see FIG. 4B) and Individual-Medical information 121 stored in database 120 (see FIG. 5).

Profile-1 is used for attending physicians (doctors). An attending physician is licensed to practice without a supervising physician, and is able to supervise trainee doctors such as residents and fellows. Profile-1 enables its holder to read an individual's name/contact, non-medical and medical information. If approved by the individual, a profile-1 holder may write (append, edit, delete) the individual's medical record. If not approved by the individual, the holder of profile-1 enables only appending to an individual's medical record. In other embodiments, without approval from the individual, the holder cannot write to the individual's record in any way. Additionally, if the individual resides in an entity (see FIG. 4B Residence_entity 431, and FIG. 7 Indiv-1-resides 2061), such as a nursing home, all attending doctors associated with the entity can write to the individual's medical record.

Profile-2A is used for health care providers having limited authority relative to a physician, such as physician assistants (PAs) and nurse practitioners (NPs), who can prescribe certain drugs and order certain tests on their own authority. PAs and NPs are often the first people in a hospital emergency department to evaluate incoming patients. Profile-2B is used for trainee doctors, such as interns, residents and fellows, that have obtained their own medical license. A trainee doctor is legally required to work under the supervision and license of an attending physician.

Profile-2C is used for trainee doctors that have not obtained their own medical license.

Profiles-2A-2C enable their holders to read an individual's name/contact, non-medical and medical information, and to append to an individual's medical information, when approved by a holder of profile-1 who has been granted write ability by the individual account holder. This is a form of inheriting access permission.

Profile-3 is used for nurses. Profile-3 enables its holder to read an individual's name/contact, non-medical and medical information. If the individual resides in an entity, all nurses associated with the entity can write to the individual's Medication Administration Record (MAR) (see FIG. 5 MAR 654), and can create a transfer note in the individual's non-medical informaiton (see FIG. 4B optional transfer_note 433) indicating, e.g., when an individual was tansferred from a nursing home to a hospital. This is a form of inheriting access permission.

Profile-4 is used for medically qualified first responders, such as emergency medical technicians (EMTs) and paramedics. Profile-4 enables its holder to read an individual's name/contact, non-medical and medical information. In this embodiment, holders of profile-4 do not require approval from a holder of profile-1A to read an individual's information, but in other embodiments, such approval may be required.

Profile-5 is used for non-medically qualified first responders, such as police, firefighters, National Guard, Federal Emergency Management Agency (FEMA) staff, United Nations (UN) Peacekeepers, and so on. Profile-5 enables its holder to read an individual's name/contact and non-medical information, but does not enable its holder to read an individual's medical information.

Profile-6 is used for good samaritan passers-by and unregistered persons who cannot be authenticated as discussed above. There are no registered holders of profile-6. Profile-6 is intended for a situation where an untrained person sees an individual in distress or collapsed. The present system advises the passerby to contact emergency assistance, but enables a passerby who provides their mobile number to learn the name of the person in distress and possibly the name and electronic contact information for their primary emergency contact, and to send a notice to the primary emergency contact, if any, of the distressed individual. As an example, a good samaritan trying to reunite a lost child with his or her guardian uses profile-6 access.

Profile-7 is used for an entity that pays for an individual or professional account, and/or serves as the residence for individuals. Profile-7 enables its holder to see, for the accounts that it pays for, the name associated with the account, and whether or not the account holder has populated their primary account. This enables the entity to remind the individual that the individual should start using their pre-paid account, a benefit of being associated with the entity. If an individual resides at the entity, the inviviudal may grant read/write ability to a profile- 7 holder associated with the entity.

Importantly, information from an individual's account is not available to anyone who is unregistered and unauthenticated, thereby protecting the privacy of the individual's information.

An entity account is used to pay for individual and/or professional accounts. For instance, a corporate employer may provide individual accounts to its employees, or an association may provide individual accounts to its members. A hospital or medical practice may provide professional accounts for its affiliated health care professionals, and may provide individual accounts for its employees.

FIG. 3B shows exemplary weights for authentication elements for different authenticatable profiles, and is discussed below in connection with the use cases. In other embodiments, different weights are used. The authentication elements in this embodiment are PRO-1-Approval 190, ID-trusted-db 191, Credit-card 192, Indiv-approval 193, Mobile-location 194. Note that the weights in each row sum to 1.0.

FIG. 3C shows exemplary scoring standards for authentication elements 190, 191, 192, 193, 194. In other embodiments, different scoring standards are used. A score for an authentication element can depend on one or more of:

information received in response to a query generated and sent by server 100;

a determination by server 100 that there are technical difficulties, typically because a response is not received to a query that was generated and sent by server 100;

a previous determination by server 100 relating to a requestor, usually stored in Access_history 899 for a registered requestor (see FIG. 6A) or in Access_history 999 for an unregistered requestor that has previously requested access (see FIG. 6B);

information stored in a record for a registered requestor; and information stored in a record for registered holder of profile-1 who is providing approval for a requestor having one of profiles 2A-2C.

In other embodiments, different factors may be used to score an authentication element. In some embodiments, a score of zero, on any authentication element having a non-zero weight, results in a determination that the requestor cannot be authenticated. Determining an authentication score for an unregistered requestor is discussed below (see FIG. 8B step 280, and the use cases).

Information records used by server 100 will now be discussed.

An individual's name/contact information is shown in record 111 of FIG. 4A, their non-medical information is shown in record 112 of FIG. 4B, and their medical information is shown in record 121 of FIG. 5. The individual's PIN is used as an index to find the correct instances of records 111, 112 and 121.

A registered professional's account information is shown in record 131 of FIG. 6A; this record is created during a set-up phase (not shown). An unregistered and authenticated professional's account information is shown in record 132 of FIG. 6B; this record is created by server 100 during authentication. An entity's account information is shown in record 141 of FIG. 7.

It will be understood that some of the fields discussed below may be repeated as often as needed to properly represent information. For example, if an individual or professional wishes to register multiple credit cards with server 100, then the appropriate fields appear for each of the credit cards.

FIG. 4A shows record 111 of individual name/contact information database 105. Each individual account corresponds to a single instance of record 111. Record 111 includes:

PIN field 400 for the individual's PIN;

Honorific field 410 for the individual's honorific (Mr./Ms./Dr. etc.);

Name field 401 for the individual's name;

Emg_Contact field 402 for the name of the individual's primary emergency contact;

Emg_Contact_phone field 403 for the telephone number of the individual's primary emergency contact;

Emg_Contact_email field 404 for the email address of the individual's primary emergency contact;

Access_history field 405 for holding a record of who, other than the individual, has accessed record 111, typically represented as PRO_ID/date/start_time/end_time/name.

FIG. 4B shows record 112 of individual non-medical database 110. Each individual account corresponds to a single instance of record 112. A field not visible except to the account owner is indicated by double carets (<<...>>). An optional field is indicated by square parends ([...]). Record 112 includes:

PIN field 400 for the individual's PIN;

<<Password field 406>> for the individual's password;

<<Security question filed 407>> required if the user wants to be reminded of his/her password;

<<Consent code field 408>> for the individual's consent code, that is, a code provided by the individual to a professional health care provider to enable the professional health care provider to access the individual's name/contact, non-medical and medical information (but not the information for a linked primary account, or any secondary accounts) in accordance with the profile of the health care professional;

Secondary field 413 to indicate if this account is a primary or secondary account;

Birthdate field 414 providing the birthdate of the individual;

Age field 416, automatically computed by server 100 at each access based on birthdate field 414;

Gender field 418 providing the gender, male or female, of the individual;

Height field 420 providing the individual's height;

Weight field 422 providing the individual's weight;

Face_photo field 424 providing at least one face image for the individual;

Identifying_char_text field 426 providing any identifying characteristics for the individual, such as tattoos, birthmarks, amputations etc.;

Identifying_char_image field 428 providing an image of the identifying characteristics of the individual;

Residence_address field 430 providing the residence address of the individual, typically street, city, state and zip code, and possibly street number, apartment number, residence name;

Residence_entity field 431 identifying the type of residence of the individual, such as single-family home, apartment, dormitory, assisted living facility etc.;

Residence_phone field 432 providing the home phone number of the individual;

[Transfer_note field 433] indicating if the individual has been transferred from an assisted living residence to a hospital and the circumstances warranting the transfer;

Mobile_phone field 434 providing the individual's mobile phone number;

Occupation field 440 providing the individual's occupation;

Employer field 442 providing the name of the entity that employs the individual;

Employer_contact field 443 providing the name of a contact for the individual, such as the individual's supervisor;

Employment_address field 444 providing the address of the individual's employer;

Employment_phone field 446 providing the telephone number of the employer, or of the employer contact;

Spouse_Name field 452 for the name of the spouse of the individual, if any;

Dependant_Name field 454 for the name of a dependent of the individual, if any. This field has as many instances as there are instances of dependents of the individual;

Dependant_Relation field 456 indicating the relationship of the dependent to the individual, e.g., child, parent, etc;

Pet_Type field 460 indicating the type of pet, if any, of the individual. This field has as many instances as there are instances of pet types, e.g., dog, cat, hamster and so on. This information helps diagnose an individual's illness;

Religion field 470 indicating the religion of the individual, which may affect notice regarding and type of medical treatment for an individual;

Legal_Power_Type field 480 indicating the type of legal power, if any, such as a health care proxy or a power of attorney, that an individual has authorized. There is one instance of this field for each type of legal power;

Legal_Power_Name field 482 indicating the name of the holder of the legal power;

Legal_Power_Relation field 484 indicating the relationship of the holder of the legal power to the individual;

Legal_Power_Phone field 486 indicating the phone number of the holder of the legal power;

Legal_Power_Email field 488 indicating the email address of the holder of the legal power;

Legal_Power_Notif field 490 indicating whether the holder of the legal power should be automatically notified when the individual's medical information is accessed, and if so, how (e.g., text message, robocall);

Legal_Power_image field 492 indicating an image file with a scanned image of the legal power;

Emg_Contact_Name field 500 indicating a secondary emergency contact for the individual, other than the primary emergency contact in record 111 of FIG. 4A; there are as many instances of this field as there are instances of secondary emergency contacts for the individual;

Emg_Contact_Relation field 502 indicating the relationship of the emergency contact to the individual, e.g., spouse, parent, friend, co-worker;

Emg_Contact_Phone field 504 indicating the phone number of the emergency contact;

Emg_Contact_Email field 506 indicating the email address of the emergency contact;

Emg_Contact_Notif field 508 indicating whether the emergency contact should be automatically notified when the individual's medical information is accessed, and if so, how (e.g., text message, robocall);

Insurance_Med_1 field 510 indicating a first provider of insurance for the individual, such as insurance available from the individual's employer, including, as appropriate, name, policy number, member number, phone number for the insurer and website for the insurer;

Insurance_Med_2 field 512 indicating, if any, a second provider of insurance for the individual, such as insurance available from the individual's spouse's employer;

Insurance_Dental field 514 indicating, if any, a provider of dental insurance for the individual;

Insurance_Vision field 516 indicating, if any, a provider of optical insurance for the individual;

Insurance_Prescrip field 518 indicating, if any, a provider of prescription drug insurance for the individual;

Insurance_Other field 520 indicating, if any, another provider of insurance for the individual;

Payment_source field 530 indicating who is responsible for paying for the individual to be a member of the information system, such as the individual or an entity;

Payment_method field 532 indicating how invoices are to be paid, e.g., by credit card, automatic bank account debit, electronic invoice and so on;

<<Payment_acct field 534>> indicating the account number, if any, of the credit card or bank account indicated in field 532;

<<Payment_code field 536>> indicating the credit card three or four digit code, or the bank routing number, as indicated in field 532;

Linked_PIN_1 field 540 indicating any individual account bearing a linked relationship to this individual's account; this field is repeated as many times as needed;

Secondary_PIN_1 field 550 indicating any individual account bearing a secondary relationship to this account, and whether this account is or is not a master relative to the secondary account; this field is repeated as many times as needed;

Notification_Prefs field 560 indicating how the individual wishes to be notified of access attempts for record 112, such as text message, email message, robocall and so on;

Access_history field 570 for holding a record of who, other than the individual, has accessed record 112, typically represented as PRO_ID/date/start_time/end_time/name.

FIG. 5 shows record 121 of individual medical database 120. Each individual account corresponds to a single instance of record 121. Record 121 includes:

PIN field 400 for the individual's PIN;

Blood_type field 605 for the individual's blood type;

Allergies field 610 for the individual's allergies, if any, with as many allergy fields as needed to represent the individual's allergies;

Current_Med_condition_1 field 620 indicating a first medical condition, if any, that the individual currently has;

Current_Med_condition_2 field 622 indicating a second medical condition, if any, that the individual currently has, with additional instances of this field for any additional medical conditions that the individual currently has;

Past_Medical_condition_1 field 624 indicating a second medical condition, if any, that the individual previously had, usually in the form of: operation-type/body-part/date/additional-info;

Past_Medical_condition_2 field 626 indicating a second medical condition, if any, that the individual previously had, with additional instances of this field for any additional medical conditions that the individual previously had;

Past_Surgery_1 field 628 indicating a previous surgery, if any, that the individual had;

Past_Surgery_2 field 630 indicating another previous surgery, if any, that the individual had, with additional instances of this field for any additional surgeries that the individual previously had;

Special_requirements field 640 indicating a special requirement, if any, that the individual has, usually in the form type/frequency/need/avoid, with additional instances of this field for any additional requirements;

Family_history field 645 indicating any major medical events in the lives of the individual's immediate family, usually in the form name/relationship/medical-event/date;

Medication_1 field 650 indicating a first medication, if any, that the individual is currently taking, usually in the form of medication name/dosage amount/dosage frequency, such as to take if needed and any relevant indications;

Medication_2 field 652 indicating a second medication, if any, that the individual is currently taking, with additional instances of this field for any additional medications that the individual is currently taking;

Medication_Admin_Record field 654 indicating, for an individual in an assisted living facility, their MAR;

Alcohol_history field 660 indicating the alcohol history of the individual, in the form of quantity of alcohol per week, and duration (start year, end year);

Tobacco_history field 670 indicating the tobacco usage history of the individual, in the form of number of cigarettes per day, and duration (start year, end year);

Recreational_drug_history field 680 indicating the recreational drugs used by the individual, such as marijuana, cocaine, heroin, that the individual has been using, in the form of substance/quantity per day/start year/end year;

Advance_directive_txt field 690 indicating the organ donation wishes of the individual;

Advance_directive_image field 692 providing a scan of the legal form representing the individual's organ donation instructions;

Immunization_history field 700 indicating immunizations administered to the individual;

Travel_history field 710 indicating where the individual has travelled, and when, which is helpful in diagnosing whether an individual is part of a disease outbreak;

Other_social field 720 indicating other social events that may be relevant to the user's medical condition;

PCP field 730 providing, for the individual's primary care physician, the physician's name, phone number, email address, fax number and physical address;

Dentist field 732 providing, for the individual's dentist, the dentist's name, phone number, email address, fax number and physical address, and date of last treatment;

Optometrist field 734 providing, for the individual's optometrist, the optometrist's name, phone number, email address, fax number and physical address, and date of last treatment;

Doctor_specialist_1 field 736 providing, for the individual's first specialist, if any, the specialist's name, phone number, email address, fax number and physical address, and date of last treatment;

Doctor_specialist_2 field 738 providing, for the individual's second specialist, if any, the specialist's name, phone number, email address, fax number and physical address, and date of last treatment, with additional instances of this field as needed for all of the individual's specialists;

Pharmacy field 740 indicating the name, address and phone number of the individual's preferred pharmacy;

Lab_result_1 field 750 indicating a first lab result and date, if any, for the individual;

Lab_result_2 field 752 indicating a second lab result and date, if any, for the individual;

Xray_1 field 754 providing a first x-ray, if any, for the individual, along with the body part, date, and unusual condition (if any);

Xray_2 field 756 providing a second x-ray, if any, for the individual, along with the body part, date, and unusual condition (if any);

Other_image field 758 providing another image, if any, for the individual, along with the body part, date, and unusual condition (if any);

Electrocardiogram field 760 providing an electrocardiogram, date, and unusual conditions (if any) for the individual;

Notification_Prefs field 770 indicating any additional notification information for the individual, such as persons to be notified of acc ss, but who are not emergency contacts;

Access_history field 780 for holding e a record of who, other than the individual, has accessed record 121, typically represented as PRO_ID/date/start_time/end_time/name.

FIG. 6A shows record 131 of professional database 130. Record 131 represents the account of a registered health care professional, and is created during a set-up phase (not shown). Record 131 includes:

PRO_ID field 800 for the professional's PRO_ID (username);

Password field 810 for the password corresponding to the PRO_ID;

Security_question_1 field 812 containing a first security question that must be correctly answered for server 100 to send the PRO_ID and password to the professional;

Security_question_2 field 814 optionally containing a second security question that must be correctly answered for server 100 to send the PRO_ID and password to the professional;

PRO_Type field 815 indicating the profile type of the professional;

Entity_affiliation field 817 indicating, if any, an entity affiliation of the professional, such as a hospital that the professional is able to practice at;

Face_photo field 820 containing a face photograph of the professional in any suitable image format, such as .jpg, .gif and so on;

Biometric field 822 optionally containing a type of biometric of the professional, such as a voiceprint, and a file of the biometric itself;

Honorific field 828 for the honorific of the professional (Mr./Ms./Dr. and so on);

Name field 830 for the name of the professional, including any nicknames;

Medical_speciality field 832 for the medical specialty of the professional, with additional fields for each additional medical specialty of the professional;

[Default_PRO field 837] optionally indicating a holder of profile 1 from whom access permission should be requested for each individual account that the professional wants to access;

[PreapprovedBy_PRO field 839] optionally indicating a holder of profile 1 that has preapproved the professional to access all individual accounts;

Mobile_phone field 840 for the mobile phone number of the professional;

Personal_email field 842 for the email address of the professional;

Entity_phone field 843 indicating a phone number, if any, for an entity that sponsors the professional;

Entity_sponsor field 844 indicating an entity, if any, that sponsors the professional;

Occupation field 845 providing the occupation of the professional;

Employer field 850 providing the name of the employer of the professional;

Employment_address field 852 providing the address of the employer of the professional;

Employment_phone field 854 providing the phone number of the employer of the professional;

Employment_email field 856 providing the email address of the professional as supplied by the employer of the professional;

Accepted_insurance field 860 indicating the insurance plans accepted by the professional;

Residence_address field 865 indicating the residence address of the professional;

Residence_phone field 870 indicating the residence phone number of the professional;

Medical_license_state field 875 indicating the state in which the professional is licensed to practice. There is one instance of this field for each state that the professional is licensed to practice in;

Medical_license_number field 877 indicating the state license number for the professional;

National_Provider_Index field 879 indicating, for certain professionals, their NPI number;

Credit_card_1 field 885 indicating a first credit card and three or four digit authorization code for the professional;

Credit_card_2 field 890 indicating a second credit card and three or four digit authorization code for the professional;

Payment field 895 indicating who is responsible for paying for the professional's account, the payment method and payment account, and any other billing details;

Notification_Prefs field 897 indicating how the professional wishes to be notified when an information access is made using their account (assists in fraud detection), such as via text message, email or robocall;

Access_history field 899 for holding a record of which individual accounts have been accessed by this professional, typically represented as PIN/date/start_time/end_time/name.

Figure 8A:
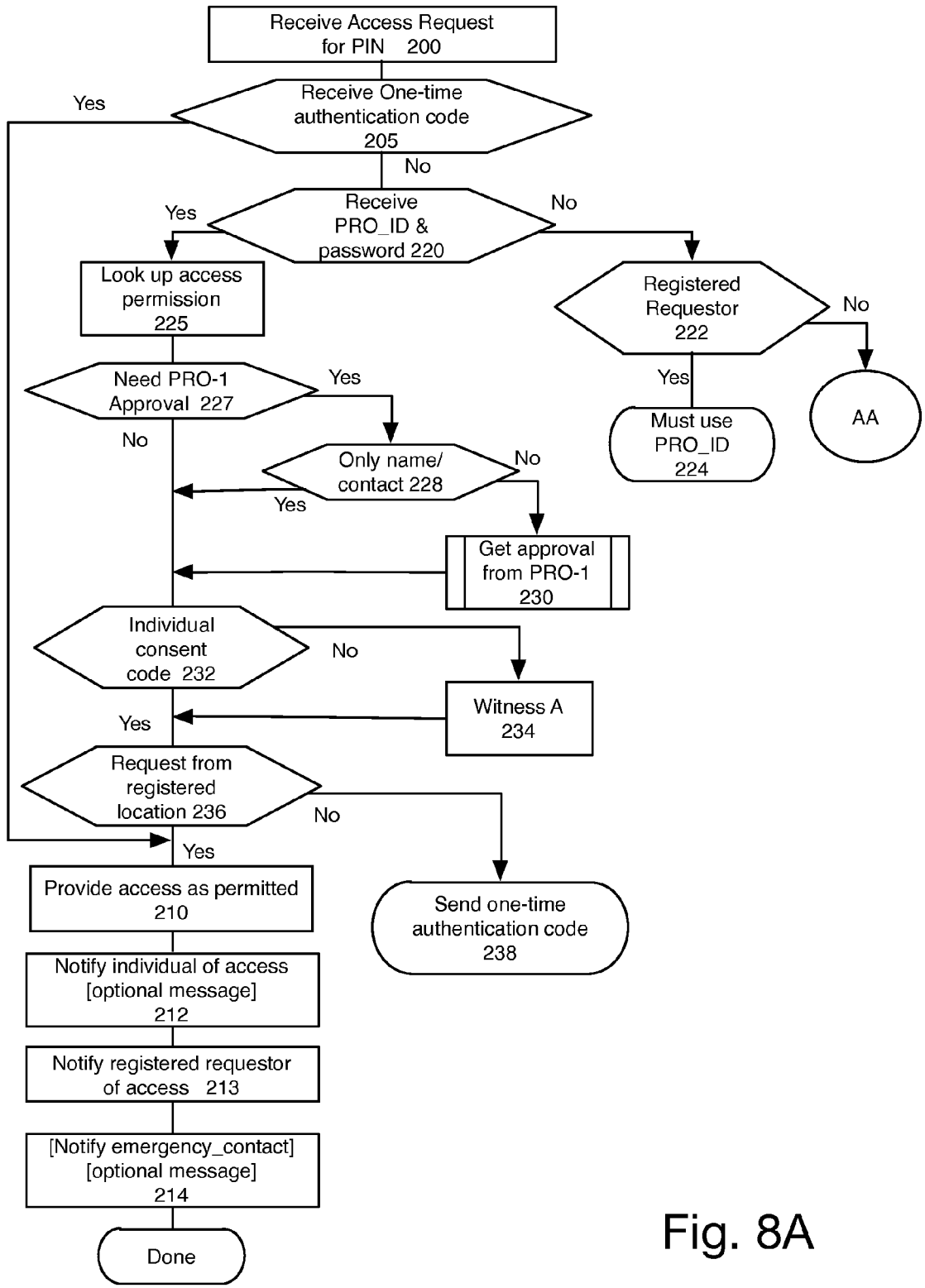
FIGS. 8A-8C are a flowchart showing operation of the present invention.
Figure 8B:
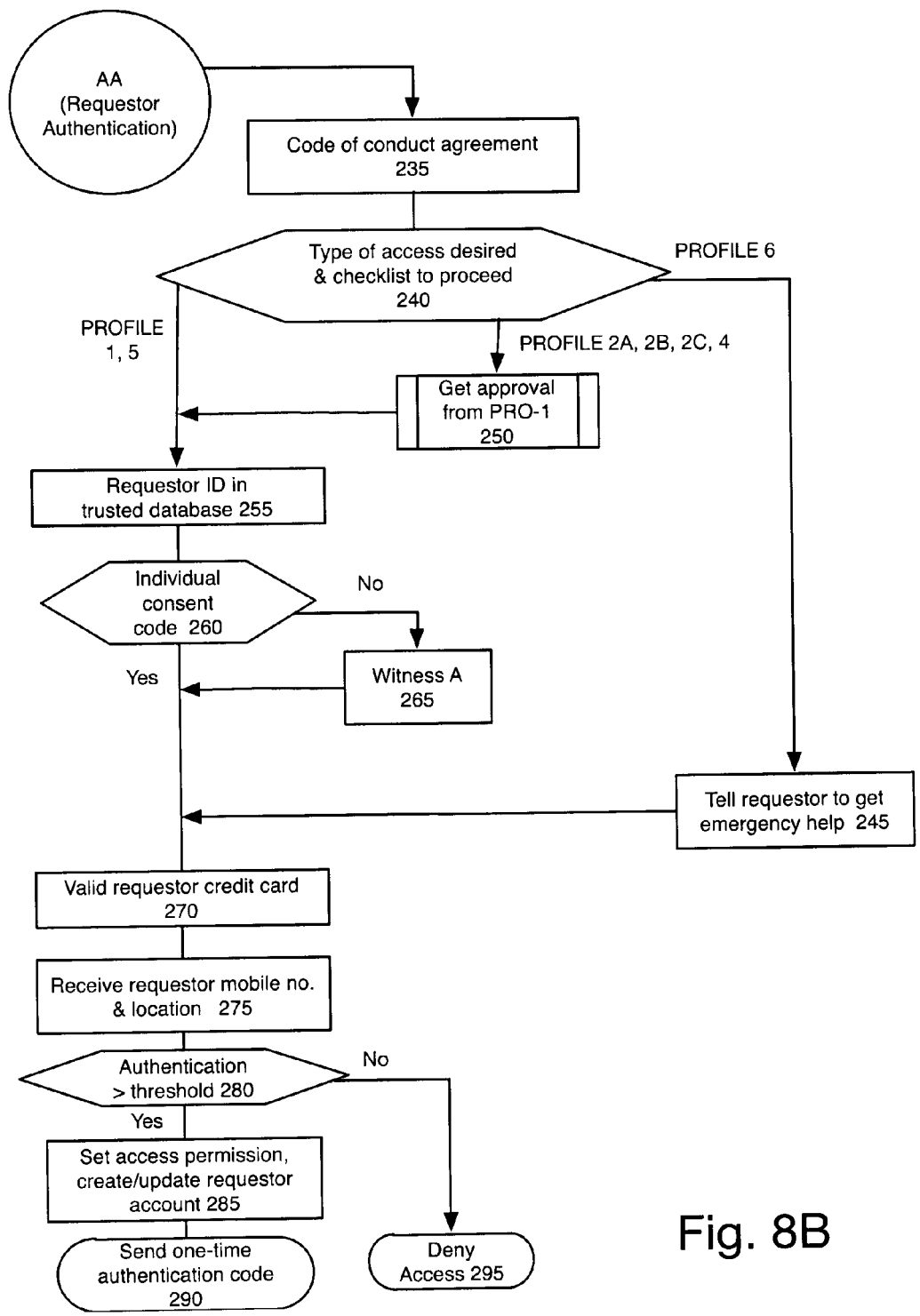

FIG. 6B shows record 132 of professional database 130. Record 132 represents the temporary access of an authenticated but unregistered health care professional, and is created in response to an access request from the unregistered health care professional (see FIG. 8B step 285 and FIG. 8C step 345). Record 132 includes:

PRO_unreg field 900 for a temporary username assigned by server 100, but not known to the unregistered professional. In this embodiment, the mobile phone number of the unregistered requestor is used as his/her PRO_unreg username;

One-time_code field 905 for holding a one-time access code assigned by server 100 (see FIG. 8B step 290);

One-time_password field 907 for holding a password, if any, assigned by server 100;

One-time_duration field 909 for indicating the expiration time of the one-time code. The remaining fields in record 132 are similar to the corresponding fields in record 131, and for brevity, are not discussed.

FIG. 7 shows record 141 of entity database 140, created during a set-up phase (not shown). Record 141 includes:

Entity_ID field 2000 for the entity identification (username);

Password field 2005 for the password;

Security_question field 2010 for a security question that must be answered correctly, in case the entity forgets its password;

Entity_name field 2020 for the name of the entity;

Entity_address field 2022 for the address of the entity;

Entity_phone field 2024 for the phone number of the entity;

Entity_IP_address field 2026 for the Internet protocol (IP) address, if any, assigned to the entity;

Entity_TaxID field 2028 for the tax identification number of the entity;

Admin_Name_1 field 2030 for the name of a first administrative person associated with the entity;

Admin_Email_1 field 2032 for the email address of the first administrative person;

Admin_Username_1 field 2034 for a username of the first administrative person;

Admin_Password_1 field 2036 for a password of the first administrative person;

Admin_Security_Q_1 field 2038 for a security question that must be answered correctly, in case the first administrative person forgets his/her password;

Admin_Name_2 field 2040 for the name of a second administrative person associated with the entity;

Admin_Email_2 field 2042 for the email address of the second administrative person;

Admin_Username_2 field 2044 for a username of the second administrative person;

Admin_Password_2 field 2046 for a password of the second administrative person;

Admin_Security_Q_2 field 2048 for a security question that must be answered correctly, in case the second administrative person forgets his/her password;

Accepted_Insurance field 2050 indicating which insurance, if any, is accepted by the entity;

Individual_account_1 field 2060 indicating a first individual account (PIN), if any, that is associated with the entity, such as for payment purposes;

Individual_account_2 field 2062 indicating a second individual account (PIN), if any, that is associated with the entity, such as for payment purposes;

Individual_1_resident field 2061 indicating a first individual account (PIN), if any, for an individual that resides at the entity;

Individual_2_resident field 2063 indicating a second individual account (PIN), if any, for an individual that resides at the entity;

PRO_account_1 field 2070 indicating a first professional (PRO_ID), if any, that is associated with the entity, and the type of association (e.g., payment, sponsorship, access privileges);

PRO_account_2 field 2072 indicating a second professional (PRO_ID), if any, that is associated with the entity, and the type of association (e.g., payment, sponsorship, access privileges);

Payment_max field 2080 for indicating the maximum payment, if any, authorized by the entity;

Invoice_type field 2090 for indicating how the entity wishes to be invoiced, e.g., electronically, by debiting an account, by charging a credit card, and so on;

Invoice_recipient_name field 2091 indicating a name of the primary recipient of the entity's invoice;

Invoice_recipient_email field 2092 indicating an email of the primary recipient;

Invoice_recipient_phone field 2093 indicating a phone number of the primary recipient;

Invoice_recipient_addr field 2094 indicating an address of the primary recipient;

Alt_invoice_recip_name field 2095 indicating a name of an alternate recipient, if any, of the entity's invoice;

Alt_invoice_recip_email field 2096 indicating an email of the alternate recipient;

Alt_invoice_recip_phone field 2097 indicating a phone number of the alternate recipient;

Alt_invoice_recip_addr field 2098 indicating an address of the alternate recipient.

During a set-up phase (not shown), each individual member of the medical information system populates their name/contact, non-medical and medical records, agrees to terms of use and a code of conduct, and receives a personal identification number (PIN) that uniquely identifies their records relative to other records in the medical information system. The PIN can be an alphanumeric code including ASCII symbols, it is not restricted to the numeric characters 0-9.

During a set-up phase (not shown), each professional populates their record, agrees to a code of conduct for the medical information system, and receives a professional identification number (PRO_ID, see FIG. 6A field 800) that uniquely identifies their record relative to other records in the medical information system. The PRO_ID can be an alphanumeric code including ASCII symbols, it is not restricted to the numeric characters 0-9. In one embodiment, part of the information is verified with third-party sources during set-up. In another embodiment, part of the information is verified each time the professional wishes to access an individual's record. The set-up process may be different for different types of professionals.

In one embodiment, a trainee doctor must receive approval from an attending doctor for each access of an individual's name/contact, non-medical and/or medical information, so the set-up process for an attending doctor is stricter, for instance, requiring that the attending doctor provide a biometric such as a fingerprint, signature, spoken utterance, iris scan, heartbeat signature, or face photograph, that is then stored (see FIG. 6A biometric 822) and compared with a similar biometric provided with each operational approval. Alternatively, a secret number may be mailed via paper mail to the attending doctor's address, and must be entered by the attending doctor to complete registration. In some embodiments, all professionals must provide a biometric.

An optional field, indicated by square parends [ ] in FIG. 6A, for indicating a default attending doctor associated with a trainee doctor is Default_PRO 837.

An optional field, indicated by square parends [ ] in FIG. 6A, for indicating a pre-approved attending doctor associated with a trainee doctor is PreapprovedBy_PRO 839.

In embodiments where trainee doctors can have access pre-approved by an attending doctor, or be associated with an attending doctor who provides permission for each access, that attending doctor must agree to inclusion in the trainee doctor's record.

During a set-up phase (not shown), each entity is linked with records for the individuals or professionals for whom it pays, referred to as the entity's members. The payment is provided to the medical information system, for usage thereof. In some embodiments, the entity creates a mostly unpopulated record for each of its members, which serves as one form of validation of the identity of the member.

Usage database 150 contains audit trail information generated by server 100.

Figure 8C:
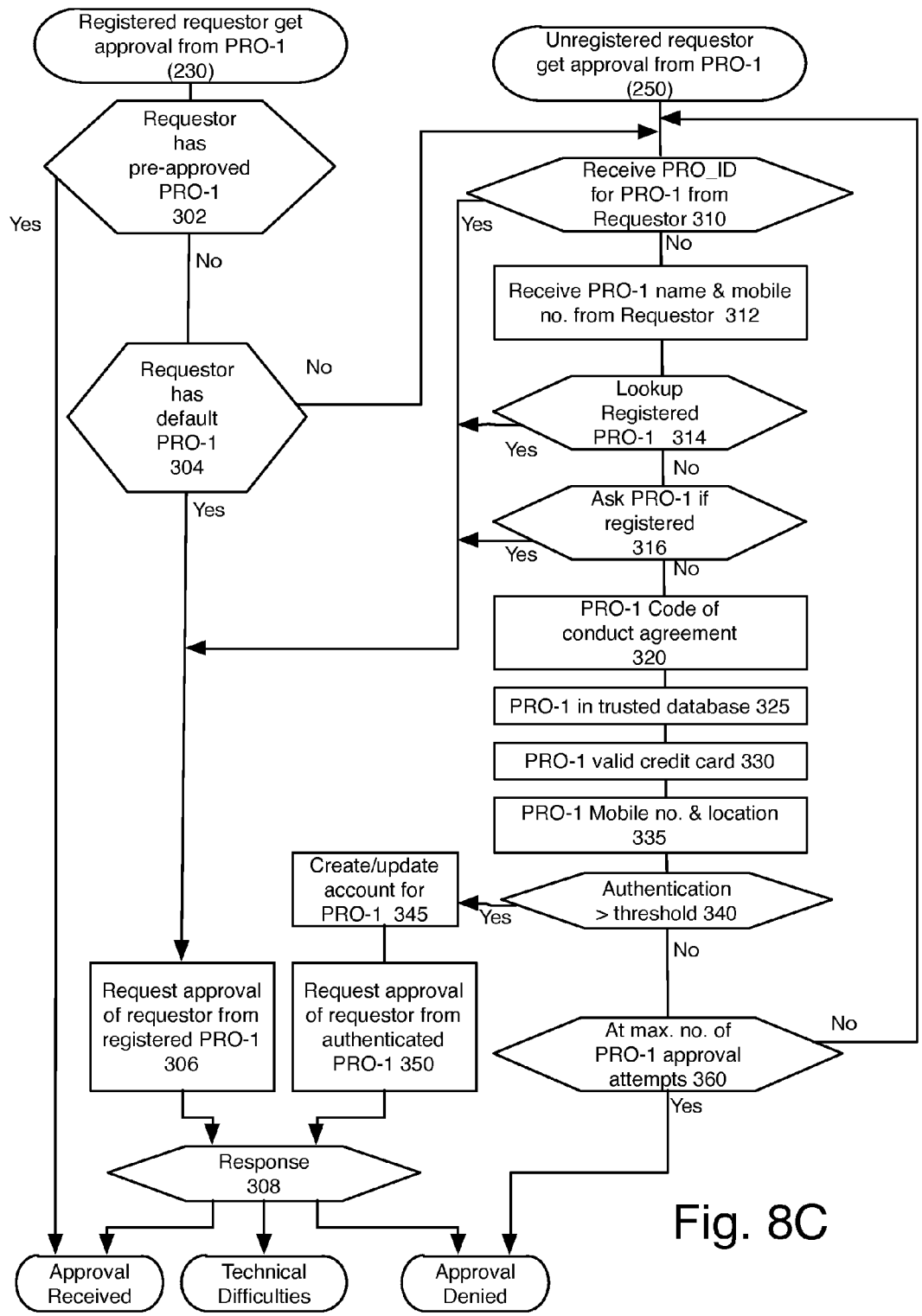

FIGS. 8A-8C comprise a flowchart showing operation of server 100. The illustrated embodiment includes five authentication tests: identity, transaction, individual's approval, location, and, for a trainee doctor, approval from an attending doctor, that is, a holder of profile-1 due to either registration or authentication. In other embodiments, the sequence of these tests is altered. In still other embodiments, the number of authentication tests is altered. As discussed below, each type of authentication can be varied. The intent is that the strength of authentication be reasonably high, subject to the authentication not being too onerous to conduct during an emergency.

At step 200 of FIG. 8A, server 100 receives an access request from a requestor including a PIN for an individual.

At step 205, server 100 checks whether the access request includes a one-time code that has not expired. Generation of a one-time code is discussed below. If so, processing continues at step 210. If not, processing continues at step 220.

At step 210, server 100 provides access, to the requestor who now becomes the accessor, to the individual's name/contact, non-medical and medical information associated with the PIN, in accordance with the access permission granted by the one-time code, for the time duration granted by the one-time code. Server 100 updates the individual's records to reflect who accessed them, and for how long, and similarly updates the accessor's record to show whose records were accessed and for how long. Server 100 also reflects this activity in audit trail database 150.

At step 212, upon the start of access to an individual's records within the granted time duration, server 100 generates a notice and notifies the individual in accordance with the individual's notification preferences (see FIG. 4B element 560). The notice may be provided by one or more of the following: a text message to a mobile phone, an email, a fax, a spoken voicemail message, or other form of message that can be generated by server 100 and promptly delivered. In other embodiments, the notice is sent upon completion of access to an individual's records. The professional may include an optional message, in addition to the message automatically generated by server 100, such as "Your medication list has been updated to include Xanax, please review." For a registered requestor, the notice contains at least the name of the requestor and the sponsoring entity's phone number (see FIG. 6A field 843); for an unregistered requestor, the notice contains at least the name of the requestor and their mobile phone number (see FIG. 6B field 940). If the registered requestor lacks a sponsoring entity, then the registered requestor's phone number is provided.

At step 213, server 100 generates a notice and notifies a registered requestor in accordance with the requestor's notification preferences (see FIG. 6A element 897 and FIG. 6B element 997). This is helpful for quickly detecting unauthorized accesses.

At step 214, server 100 checks whether the individual record has emergency contacts in record 112 that the individual wants automatically notified, in addition to the contact specified in record 111, and if so, prepares a notice in one or more of the manners described at step 212, then delivers the notice to the emergency contact(s) (see FIG. 4A element 404 and FIG. 4B element 508). The professional may include an optional message, in addition to the message automatically generated by server 100.

Processing is complete.

At step 220, server 100 checks whether the access request includes a registered PRO_ID and corresponding password. If so, processing continues at step 225. If not, processing continues at step 222.

At step 225, server 100 determines the access permission for the health care professional associated with the PRO_ID. Generally, this includes looking up the profile type of the professional (see FIG. 6A element 815 and FIG. 6B element 915) and the professional's entity affiliation (see FIG. 6A element 817), and the access permission and entity affiliation associated with individual. It will be recalled that some individuals reside in an entity, and if the professional is also associated with the entity, then the professional thereby inherits access permission to the individual's name/contact, non-medical and medical information in accordance with the professional's type of profile. Server 100 includes its determination of access permission as part of its audit trail database 150.

At step 227, server 100 checks whether the professional requesting access needs approval from another professional, as in the case of trainee doctors. If not, processing continues at step 232.

If, at step 227, the professional requesting access must obtain approval from another professional, at step 228, server 100 checks whether the requestor seeks only the name/contact information for an individual. If so, processing continues at step 232 with access restricted to the individual's name/contact information. Otherwise, processing continues at step 230, shown in detail in FIG. 8C. At the conclusion of processing in FIG. 8C, processing continues at step 232 of FIG. 8A, with restrictions based on the PRO_ID record, if any, and with access granted for a fixed time duration, such as twenty-four hours. At the end of that fixed time duration, the professional may request access again, which will trigger notifications at steps 212, 214.

At step 232, server 100 checks whether the individual's consent code (see FIG. 4B consent code 408) has been provided, typically by the individual verbally telling it to the professional who in turn provides it to system 100. If so, processing continues at step 236. Step 232 is an individual approval test. If not, at step 234, a first witness ("witness A") provides consent on behalf of the individual (see discussion below of FIG. 8B step 265). Preferably, the first witness is a friend or family relation of the individual.

At step 236, server 100 determines if the request for access was made from a registered location. For example, if the request was made via PC 25, the request has an IP address associated with registered entity 20. This is because registered entity 20 operates a local area network, with or without wireless connections, that bundles Internet traffic from its local area network to a network interface that has an IP address. Step 236 is a location authentication test. In this embodiment, it is assumed that a request originating from a registered location is highly likely to be genuine, and so is granted, and processing continues at step 210. In some embodiments, step 236 is omitted.

If, at step 236, the request is not from a registered location, then at step 238, server 100 sends a one-time access code to the mobile phone associated with the professional. See discussion below of step 290 of FIG. 8B.

At step 222, server 100 is processing an access request lacking a PRO_ID. Server 100 inquires if the requestor is registered. If the requestor is registered, at step 224, server 100 informs the requestor that they must provide their PRO_ID and password, and, in some embodiments, offers to send the PRO_ID to the requestor's mobile phone, if the requestor's phone number matches one of the registered mobile phone numbers in professional database 130. This helps prevent fraudulent requestors from gaining access using a registered professional's name. If the requestor is unregistered, that is, lacks a PRO_ID, processing continues at step 235 of FIG. 8B, to authenticate the unregistered requestor.

At step 235 of FIG. 8B, server 100 presents the code of conduct and terms of use for the medical information system to the requesting party, who must agree for processing to continue.

At step 240, server 100 asks the requestor what type of access they want, that is, which profile the requestor believes he/she will qualify for, and provides, to the requesting party, a checklist of what will be required to proceed, and the timeframe available. If the requesting party cannot comply within the timeframe, then the requesting party must make a new access request. If the requestor indicates profile-1 or profile-5 type of access, processing continues at step 255. If the requestor indicates profile-2A, 2B, 2C or 4 type of access, processing continues at step 250. If the requestor indicates profile-6 type of access, processing continues at step 245.

At step 245 of FIG. 8B, server 100 tells the requestor to get emergency help, and if appropriate, provides proper local alternatives, such as "call 911". Processing continues at step 270. In embodiments where authentication for a Profile-6 type of request is based on only possession of a mobile phone, processing continues at step 275.

At step 250 of FIG. 8B, server 100 determines that the requestor must obtain approval from another professional: an attending doctor who is a holder of profile-1. Step 250 is an approval authentication test. Obtaining approval is shown in detail in FIG. 8C. At the conclusion of this step, server 100 has determined a score for PRO-1-Approval authentication element 190.

At step 255 of FIG. 8B, server 100 asks the requesting party for their name, and checks whether that name is in at least one trusted database, by querying at least one of trusted servers 60, 70, and is not already a registered professional; if the name is already registered, then an impersonation attempt might be in progress. Step 255 is an identity authentication step. At the conclusion of this step, server 100 has determined a score for ID-trusted-db authentication element 191.

For improved security, in some embodiments, server 100 chooses one of several trusted databases; since the requestor will not know which database will be used, it will be harder for the requestor to obtain suitably faked credentials to impersonate someone in a trusted database.

In some embodiments, server 100 also requires that the requesting party provide a biometric, such as a face photograph, a fingerprint, an iris scan, a heartbeat signature, a spoken utterance, or a signature, that will be compared with a biometric from a trusted database, and/or will be retained for evidence purposes.

When server 100 determines that the name is in the trusted database, server 100 stores the name as part of its audit trail, and, in some embodiments, performs a rudimentary usage check. For instance, if two parties in disparate locations are simultaneously claiming to have the same identity, then at least one of them is an impersonator. As another instance, if the number of accesses associated with a name exceeds a threshold per time period, then impersonation may be occurring. In some embodiments, server 100 may deny access to the requesting party. In other embodiments, server 100 may notify someone, such as an administrator or police officer, who can make in-person inquiries. The audit trail may also be used to market membership in the medical information system to a health care professional that has used it at least once, and possibly to an entity having health care professionals who are using the system on their own.

At step 260, server 100 asks the requesting party for the individual's consent code (see FIG. 4B element 408). If the individual's consent code is supplied, processing continues at step 267. If the individual's consent code is not supplied, typically because the individual is unconscious or cannot remember their consent code, then at step 265, a first witness ("witness A") must provide their name, relationship to the patient, physical address, mobile telephone number and e-mail address. At the conclusion of step 260 (or step 265 if executed), server 100 has determined a score for Indiv-approval authentication element 193.

At step 270, server 100 asks the requesting party for a credit card number and its associated credit card security code, and, in some embodiments, a credit card holder address, so server 100 can process a charge via credit card processor 80. The name authenticated at step 255 must be the name of the credit card holder. Alternatively, instead of a credit card, the requesting party can provide a bank routing code and account number, so that server 100 can process a debit to the account. Step 270 is a transaction authentication test. Because people usually protect their credit card and bank account information, this step makes impersonation more difficult. The amount charged or debited can be a token amount, such as one penny, or it can be a usage fee that increases with the number of times that this party uses the medical information system, to entice the party into becoming a registered health care professional. Server 100 saves the charge or debit in its audit trail, along with whether or not it was approved. At the conclusion of this step, server 100 has determined a score for Credit-card authentication element 192.

At step 275, server 100 asks the requesting party to enter a mobile telephone number, so that a one-time code can be sent to the mobile number. In some embodiments, global positioning system (GPS) location information from the mobile device must or may be provided. In some embodiments, location information, obtained using the cellular carriers' technology to triangulate positions relative to cell phone towers, for use by emergency personnel and police, is captured. In some embodiments, server 100 asks the requestor to specify their location. In some embodiments, the requesting party lacks a mobile number, such as when using a portable device that communicates via network 50, such an an iPad with WiFi access; in these cases, the Internet Protocol (IP) address of the requesting device is captured by server 100 as its location information, and the one-time code is sent to the requesting device. Step 275 is a location authentication test. The intent is to make it difficult for a remote requestor to spoof server 100. In some embodiments, server 100 checks whether the name associated with the mobile device matches the name provided at step 255. Server 100 adds the mobile number to its audit trail. At the conclusion of this step, server 100 has determined a score for Mobile-location authentication element 194.

At step 280, server 100 computes an authentication score and determines whether the computed authentication score exceeds a threshold. If so, processing continues at step 285. If not, processing continues at step 295, where access is denied. In some embodiments, step 280 is omitted; in these embodiments, a score of zero on any authentication element forces processing to step 295.

In this embodiment, the authentication decision is according to the following equation:

$$\sum_{auth-elements} weight_{auth-elements} * score_{auth-elements} > Threshold$$

where:
auth-elements includes PRO-1-Approval 190, ID-trusted-db 191, Credit-card 192, Indiv-approval 193, Mobile-location 194;
weight is given in FIG. 3B;
score is determined in accordance with FIG. 3C; and
Threshold is a predetermined value, such as the number 4.
The use cases discussed below show details of authentication decisions. In other embodiments, the authentication decision is made according to a different technique.

In other embodiments, other anti-fraud measures are incorporated in the authentication decision. For instance, if the same person requests access more than once in a five minute period, something may be wrong.

At step 285, system 100 determines access permission for the requestor, based on the access profile for which they have been authenticated. Server 100 creates an unregistered account (see FIG. 6B record 132) for the unregistered and authenticated requestor if an account does not already exist. If an account record exists, server 100 updates the record as appropriate, for instance, to indicate another credit card provided by the requestor.

At step 290, system 100 sends a text message with a one-time code for the PIN to the requesting party's mobile number. This enables the requestor to use a different device for access than for the request. The one-time code is good for a specified time duration, and then it expires. The one-time code specifies access permission for each of the name/contact, non-medical and medical records associated with the PIN, as determined at step 285.

The requestor then returns to step 200 of FIG. 8A, and provides the PIN and one-time code to server 100.

Turning to FIG. 8C, obtaining approval for a requestor from an attending physician, that is, a holder of profile-1, will now be discussed.

If the requestor is registered, so that FIG. 8C was reached from FIG. 8A step 230, processing begins at step 302.

If the requestor is unregistered, so that FIG. 8C was reached from FIG. 8B step 250, processing begins at step 310.

At step 302, server 100 determines whether the professional account of the requestor includes pre-approval from an attending physician (see FIG. 6A PreapprovedBy_PRO 839). If so, server 100 updates its audit trail to indicate that the requestor was pre-approved, and processing returns to FIG. 8A.

If the requestor was not pre-approved, at step 304, server 100 determines whether the professional account of the requestor indicates an attending physician from whom approval should be requested (see FIG. 6A Default_PRO 837). If so, processing continues at step 306. If not, processing continues at step 310.

At step 306, server 100 sends a request for approval to the attending physician indicated in the professional account of the requestor, such as a text message to the mobile phone of the attending physician, or a robocall to the mobile phone of the attending physician.

At step 308, server 100 receives a response from the attending physician that approves or denies access for the requestor. Alternatively, if a predetermined time, such as five minutes, has passed without a response from the attending physician, server 100 determines that there are technical difficulties that prevented a response from being obtained. Processing returns to FIG. 8A for a registered requestor, or to FIG. 8B for an unregistered requestor.

At step 310, server 100 checks if the requestor has provided a PRO_ID for an attending physician. If so, processing continues at step 306. If not, at step 312, server 100 receives, from the requestor, the name and mobile phone number of an attending physician (referred to as an "alleged attending physician" until authentication successfully completes).

At step 314, server 100 looks up the name and mobile phone number in database 130, to determine if the alleged attending physician is registered. If so, processing continues at step 306. If not, at step 316, server 100 asks the alleged attending physician if he/she is registered. If so, processing continues at step 306.

If the alleged attending physician is unregistered, at step 320, server 100 sends a notice to the mobile number for the alleged attending physician, along with the code of conduct and terms of use for the medical information system, who must agree for processing to continue. The alleged attending physician confirms the correctness of the information provided by the requestor at step 312, or corrects it (e.g., misspelling of the alleged attending physician's name).

Steps 325, 330, 335 are generally similar to steps 255, 270, 275 of FIG. 8B, and are not discussed here for brevity. At the conclusion of these steps, scores for the authentication elements for the unregistered alleged attending physican have been obtained.

At step 340, server 100 determines whether the alleged attending physician is authenticated, similar to FIG. 8B step 280, except that the weights shown in FIG. 3B for the row Profile 1 Approving are used. If the physician is authenticated, at step 345, server 100 creates an unregistered account (see FIG. 6B record 132) for the unregistered and authenticated attending physician if one does not exist, or if one exists, updates it as appropriate (e.g., to include another credit card provided by the physician), and processing continues at step 350. If the physician is not authenticated, processing continues at step 360.

Step 350 is similar to step 306, and will not be discussed for brevity. After step 350, processing continues at step 308.

At step 360, server 100 determines whether the requestor has reached the maximum number of attempts to obtain approval from an attending physician, such as three. If so, server 100 assumes that approval could not be obtained, and processing returns to FIG. 8A for a registered requestor, or to FIG. 8B for an unregistered requestor. Otherwise, processing returns to step 310 so that the requestor can try to obtain approval from a different attending physician.

Use Case 1: Registered Requestor

Let it be assumed that Dr. Welby is a registered attending emergency room doctor. An unconscious patient arrives in the emergency room, with a PIN for server 100 on their bracelet.

At step 200 of FIG. 8A, Dr. Welby provides the individual PIN and her PRO_ID and password to server 100 via her registered mobile phone. At step 205, server 100 takes the "no" branch to step 220, and then the "yes" branch to step 225. At step 227, server 100 takes the "no" branch to step 232, the "no" branch to step 234 where she obtains information access consent on behalf of the patient from a witness. At step 236, server 100 determines that the emergency room is a registered location and takes the "yes" branch to step 210.

At step 210, Dr. Welby determines from the individual's medical information (see FIG. 5 element 645) that the individual has a family history of cerebral aneurysm, a life-threatening medical condition that requires immediate evaluation, and orders appropriate tests. The tests are positive, and Dr. Welby begins treatment.

Meanwhile, at step 212, server 100 notifies the individual patient that Dr. Welby has accessed his records. At step 213, server 100 notifies Dr. Welby that she has just accessed an individual's information. At step 214, server 100 notifies the individual's primary emergency contact (see FIG. 4A element 404) and possibly additional contacts (see FIG. 4B elements 490, 508) that the individual's information has been accessed by Dr. Welby and her entity affiliation (see FIG. 6A element 817).

Use Case 2: Authentication of Requestor without Approval of Attending Doctor

Let it be assumed that Ms. Jones is a good samaritan who finds a lost boy at a shopping mall, and the lost boy has a PIN for server 100 on his bracelet.

At step 200 of FIG. 8A, Ms. Jones provides the individual PIN to server 100 via her unregistered mobile phone. At step 205, server 100 takes the "no" branch to step 220, and then the "no" branch to step 222, then the "no" branch to FIG. 8B step 235.

At step 235, Ms. Jones agrees to the code of conduct and terms of use. Server 100 proceeds to step 240, determines that Ms. Jones desires profile 6 access, and takes the "profile 6" branch to step 245. Server 100 suggests that Ms. Jones get emergency help if there is a medical emergency, and Ms. Jones says there is no emergency. At step 270, server 100 obtains credit card information from Ms. Jones, charges her one penny, determines that the charge was authenticated, and proceeds to step 275, where server 100 obtains the GPS location of Ms. Jones's mobile phone. At step 280, server 100 authenticates Ms. Jones because:

$$\text{weight}_{credit\text{-}card} * \text{score}_{credit\text{-}card} + \text{weight}_{mobile} * \text{score}_{mobile}\ ?>4$$

$$(0.50)*(5)+(0.50)*(4)?>4$$

$$2.5+2?>4$$

$$4.5>4$$

where the weights are obtained from FIG. 3B, the row for profile 6, and the scores are obtained from FIG. 3C, the rows for credit-card 192 and mobile-location 194.

At step 285, server 100 creates record 132 for Ms. Jones (see FIG. 6B), sets her access permission according to FIG. 3A, the row for profile 184, and at step 290, server 100 sends a one-time code to her mobile phone, good for 15 minutes.

Ms. Jones immediately returns to FIG. 8A step 200, and provides the one-time code to server 100. At step 205, server 100 takes the "yes" branch to step 210.

At step 210, Ms. Jones learns the boy's name, his emergency contact's name and the phone number for the emergency contact, and calls the boy's emergency contact.

Meanwhile, at step 212, server 100 notifies the primary account associated with the lost boy, who has a secondary account, that Ms. Jones has accessed his record, and provides Ms. Jones's name and mobile phone number to the holder of the primary account. At step 213, server 100 takes no action because Ms. Jones is not registered. At step 214, server 100 notifies the boy's primary emergency contact (see FIG. 4A element 404) that the boy's name/contact information has been accessed by Ms. Jones and provides her name and phone number.

Use Case 3: Authentication of Requestor with Approval of Attending Doctor

Let it be assumed that Dr. Huang is an unregistered resident physician without a medical license, in his third week of working in the emergency room. Last week, Dr. Welby, a registered attending physician, enabled him to use server 100 on an incoming patient. Now, a conscious patient arrives in the emergency room, complaining of severe stomach cramps. The patient knows his PIN and tells Dr. Huang, but cannot remember his consent code. The patient's girlfriend is there, too. Assume that Dr. Welby's mobile phone battery has run out of power, but she has not noticed.

At step 200, Dr. Huang provides the patient's PIN to server 100. At step 205, server 100 takes the "no" branch to step 220, and then the "no" branch to step 222, and then the "no" branch FIG. 8B step 235.

At step 235, Dr. Huang agrees to the code of conduct and terms of use. At step 240, Dr. Huang chooses profile 2C access. At step 250, server 100 proceeds to FIG. 8C step 310, where Dr. Huang provides Dr. Welby's PRO_ID. At step 306, server 100 requests approval for Dr. Huang from Dr. Welby. Dr. Welby does not respond within five minutes because her phone battery is out of power, so she never even got the request. Accordingly at step 308, server 100 determines there were technical difficulties. Returning to FIG. 8B, at step 250, server 100 determines a score for PRO-1-approval element 190 of Dr. Huang's authentication as "4" because there were technical difficulties (no response from Dr. Welby) and Dr. Huang had been approved within the past 30 days (determined by finding Dr. Huang's record 132 in professional database 130 based on his mobile number, see step 275 below, the authentication score actually is computed at step 280 below) (see FIG. 3C row 190). From FIG. 3B, row 176 for profile 2 Å, the weight of the approval element is 0.6. So far, Dr. Huang's authentication score is:

$$\text{weight}_{approval} * \text{score}_{approval} = (0.6)*(4)=2.4$$

At step 255 of FIG. 8B, server 100 does not try to look up Dr. Huang in a trusted database, because he does not have a medical license.

At step 260, server 100 determines that the patient's consent code was not provided. Instead, at step 265, the patient's girlfriend acts as a witness, providing her name, relationship, address, phone and email address. Server 100 determines a score of "4" from FIG. 3C row 193. From FIG. 3B, column 193 for profile 2C, the weight of the individual approval element is 0.2. So far, Dr. Huang's authentication score is:

$$2.4+[\text{weight}_{indiv\_approval} * \text{score}_{indiv\_approval} = (0.2)*(4)=0.8]=3.2$$

At step 270, server 100 obtains credit card information from Dr. Huang, charges him one penny and determines that the charge was authenticated. Server 100 determines a score of "5" from FIG. 3C row 192. From FIG. 3B, column 192 for profile 2C, the weight of the credit card element is 0.2. So far, Dr. Huang's authentication score is:

$$3.2+[\text{weight}_{credit\text{-}card} * \text{score}_{credit\text{-}card} = (0.2)*(5)=1.0]=4.2$$

At step 275, server 100 obtains Dr. Huang's mobile number, and uses it to identify the correct unregistered record 132 in professional database 130. However, since residents often work at multiple sites, the location of their mobile device is not used as part of authentication.

At step 280, server 100 computes the authentication score and authenticates Dr. Huang for access to the patient's information, because his score of 4.2 exceeds the threshold of 4. At step 285, server 100 sets access permission in accordance with FIG. 3A row 176, and updates Dr. Huang's record 132.

At step 290, server 100 sends a one-time code to Dr. Huang's mobile phone, good for 15 minutes.

Dr. Huang immediately returns to FIG. 8A step 200, and provides the one-time code to server 100. At step 205, server 100 takes the "yes" branch to step 210.

At step 210, Dr. Huang is able to browse the patient's medical history.

Meanwhile, at step 212, server 100 notifies the patient that Dr. Huang has accessed his record, and provides Dr. Huang's name and mobile phone number to the holder of the primary account. At step 213, server 100 takes no action because Dr. Huang is not registered. At step 214, server 100 notifies the patient's primary emergency contact (see FIG. 4A element 404) and possibly additional contacts (see FIG. 4B elements 490, 508) that the patient's information has been accessed by Dr. Huang and provides his name and mobile phone number.

Another embodiment of the present invention will now be discussed.

Figure 9:
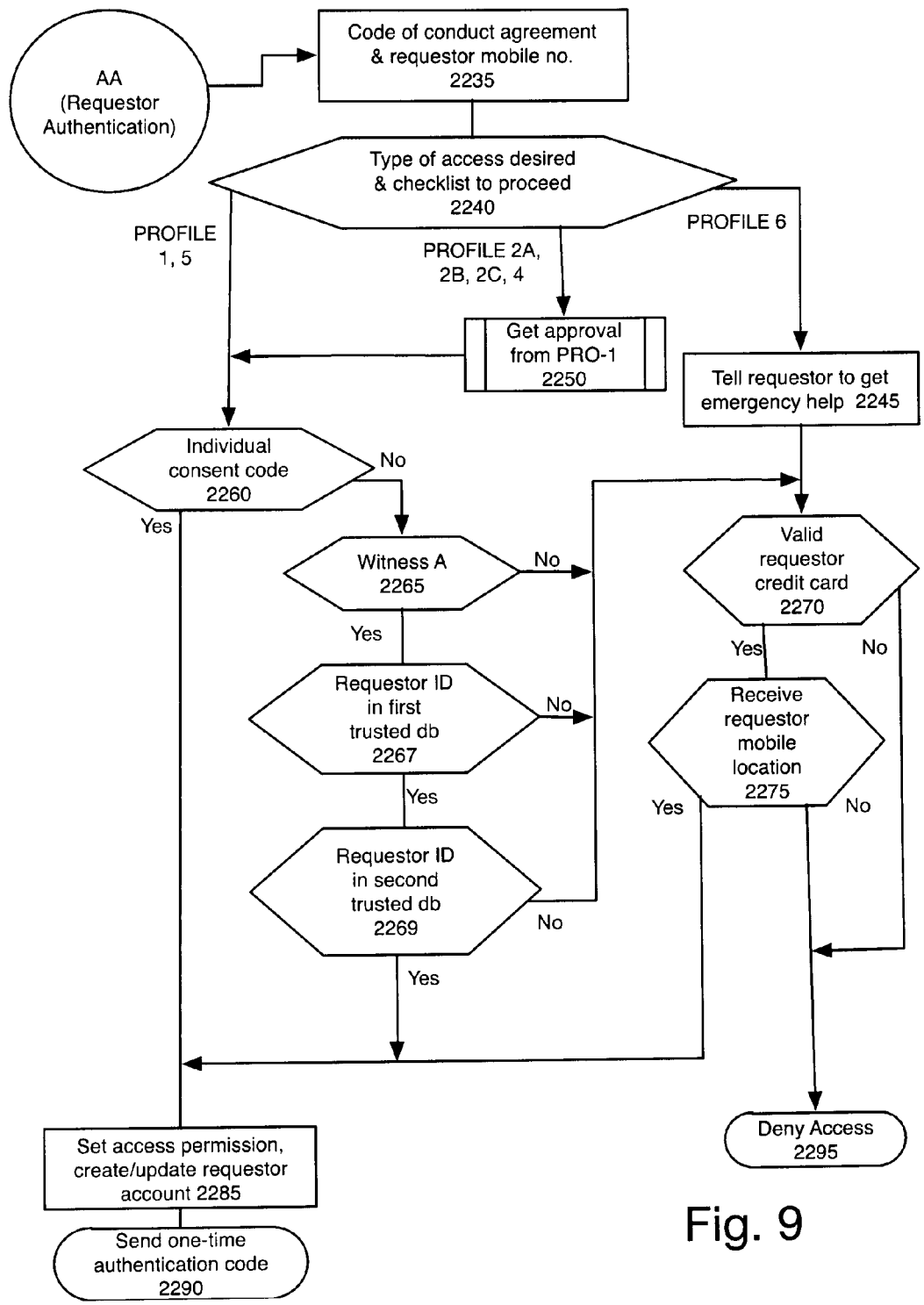
FIG. 9 is a flowchart showing operation of a second embodiment of the present invention.

FIG. 9 is a flowchart showing processing that is used in this embodiment, in lieu of the processing shown in FIG. 8B. In FIG. 9, a set of challenges or tests is presented to an unregistered requestor, then a score based on the outcome of the challenges is computed, and if the score exceeds a threshold, access is granted. In FIG. 9, a first challenge is presented, and if the unregistered requestor passes the first challenge, then access is granted immediately, otherwise, a second challenge is presented. If the unregistered requestor passes the second challenge, then access is granted immediately, otherwise, a third challenge is presented. If the unregistered requestor passes the third challenge, then access is granted immediately, otherwise, access is denied. Each challenge can be single-part or multi-part.

At step 2235 of FIG. 9, the requestor agrees to the code of conduct and provides their mobile telephone number.

Step 2240 is similar to step 240 of FIG. 8B, and will not be discussed for brevity. After step 2240, processing continues at one of step 2245, 2250 and 2260, depending on the level of access that is requested.

Step 2245 is similar to step 245 of FIG. 8B, and will not be discussed for brevity. After step 2245, processing continues at step 2270.

Step 2250 is similar to step 250 of FIG. 8B, and will not be discussed for brevity. After step 2250, processing continues at step 2260.

If at step 2240, the requestor desired profile 1 or profile 5 access, then processing continues at step 2260.

At step 2260, a first challenge is presented. The challenge is to provide the consent code associated with the individual's PIN. This is a single-part challenge. If the consent code is provided, processing continues at step 2285. If the consent code is not provided, processing continues at step 2265.

Step 2285 is similar to step 285 of FIG. 8B, and will not be discussed for brevity. After step 2285, processing continues at step 2290, which is similar to step 290 of FIG. 8B, and will not be discussed for brevity.

Steps 2265, 2267 and 2269 comprise a second challenge that is a multi-part challenge. Server 100 sets access permission in accordance with how many parts of the multi-part challenge are passed, as described below. In other words, when the requestor does not pass all of the tests for broad access, server 100 automatically converts the access request to a request for narrower access.

In a variation (not shown), if any of the parts are not passed, then server 100 goes to processing appropriate for a profile-6 type access request, that is, the unregistered requestor's broad access request is automatically converted to a narrower access request. In other variations of this embodiment (not shown), the second challenge can be a single part test using any one of the parts shown in steps 2265, 2267, 2269, or can be a multi-part test using any two of the parts shown in steps 2265, 2267, 2269 or using four or more parts.

At step 2265, the first part of the second challenge, a witness, preferably a witness who is related to the individual as a family member or a friend, must provide (i) either their PRO_ID and password and relationship to the individual (if any), or their name, relationship to the individual (if any), residence address (optional in some embodiments), telephone number and email address, (ii) must assert, such as by clicking a radio button, that they are providing consent for access to the individual's personal information in accordance with their best understanding of the individual's wishes or, if the witness does not know the individual, then the witness must assert that they are providing consent for access to the individual's personal information in accordance with the witness's own best judgment, and (iii) for witness identity verification, if the witness lacks a PRO_ID, the witness must provide a credit card number and associated credit card security code; server 100 then processes a nominal charge, such as one cent. In a variation, instead of a credit card, the unregistered witness provides a biometric, such as a face photograph, a voice sample, a fingerprint, a handwriting signature and so on. If a suitable witness cannot be found, server 100 automatically converts the access request to a profile-6 type access request, and processing continues at step 2270.

At step 2267, the second part of the second challenge, server 100 checks whether the requestor's name, provided at step 222 of FIG. 8A, is in a first trusted database. It will be appreciated that just because the requestor's name is in the database, does not mean that person in the database and the requestor are the same, because the requestor may have a non-unique name. If the requestor's name is not in the first trusted database, server 100 automatically converts the access request to a profile-5 type access request, and processing continues at step 2270. At step 2269, the third part of the second challenge, server 100 checks whether the requestor's name is in a second trusted database. If so, processing continues at step 2285. If not, server 100 automatically converts the access request to a profile-4 type access request, and processing continues at step 2270.

Steps 2270 and 2275 comprise a third challenge that is a multi-part challenge. If any of the parts is not passed, then server 100 denies access to the unregistered requestor. In variations of this embodiment, the third challenge can be a single part test using any one of the parts shown in steps 2270 and 2275, or can be a multi-part test using an additional part (not shown).

At step 2270, the first part of the third challenge, server 100 obtains a credit card number from the requestor and charges a fee to the requestor. The fee may be nominal, such as one cent, or may be some larger amount to encourage registration. If the charge is declined, processing continues at step 2295.

At step 2275, the second part of the third challenge, server 100 obtains the location of the mobile device of the unregistered requestor, in similar manner as at step 275 of FIG. 8B. If the location cannot be automatically obtained, then the unregistered requestor is asked to manually enter their physical address. If a location or manual address is not provided, then processing continues at step 2295. If a location or manual address is provided, processing continues at step 2285.

Step 2295 is similar to step 295 of FIG. 8B, and will not be discussed for brevity.

Although illustrative embodiments of the present invention, and various modifications thereof, have been described in detail herein with reference to the accompanying drawings, it is to be understood that the invention is not limited to these precise embodiments and the described modifications, and that various changes and further modifications may be effected therein by one skilled in the art without departing from the scope or spirit of the invention as defined in the appended claims.

What is claimed is:

1. A method for providing, to a requestor, emergency access to confidential information of an individual without access consent from the individual, the requestor not previously registered to access the confidential information, the requestor being other than the individual, comprising:

receiving, at a first computer, a request for the confidential information from the requestor, and an indication of a type of confidential information desired by the requestor;

determining, by the first computer, that the requestor is unregistered;

obtaining, by the first computer, information about the requestor from second and third computers; the first, second and third computers being operated by respectively different and independent entities;

determining, by the first computer, an authentication score for the requestor based on the information obtained from the second and third computers by (i) assigning a first score to the information obtained from the second computer, (ii) assigning a second score to the information obtained from the third computer, (iii) multiplying the first score by a first weighting number to obtain a first weighted score, (iv) multiplying the second score by a second weighting number to obtain a second weighted score, and (v) adding the first and second weighted scores to generate the authentication score;

checking, by the first computer, whether the type of confidential information requires an approval from a person having a specified credential;

after receiving, at the first computer, approval from the person having the specified credential, then providing, from the first computer to the requestor, access to the confidential information of the individual without access consent from the individual when the authentication score exceeds a predetermined threshold; and sending, from the first computer to a contact for the individual, information about the requestor;

whereby the confidential information of the individual is available without the access consent of the individual only after authentication of the requestor by the first computer.

2. The method of claim 1, wherein the information about the requestor from the second and third computers includes at least two of:

(i) confirmation that a name of the requestor is in a database maintained by a governmental entity;

(ii) confirmation that a charge to a credit card number succeeded, the credit card number having been provided by the requestor to the first computer; and (iii) a location of the requestor obtained by the first computer from a device associated with the requestor.

3. The method of claim 1, wherein access to the confidential information is provided based on a profile chosen from a set of profiles in accordance with the authentication score.

4. The method of claim 1, further comprising receiving, at the first computer, information about a witness prior to the step of providing access to the confidential information.

5. The method of claim 1, wherein the information about the requestor includes (i) a first confirmation that a name of the requestor is in a first database at the second computer, and (ii) a second confirmation that the name of the requestor is in a second database at the third computer.

6. The method of claim 1, further comprising receiving, at the first computer, a message from the requestor, and wherein the step of sending information to the contact for the individual includes sending the message received from the requestor.

7. The method of claim 1, further comprising creating, by the first computer, a registration account for the requestor.

8. The method of claim 1, further comprising receiving, at the first computer, a phone number from the requestor; and wherein the step of sending information to a contact for the individual includes sending the phone number of the requestor.

9. The method of claim 8, further comprising (a) sending a one-time code from the first computer to the phone number received from the requestor; and (b) receiving, at the first computer, the one-time code before providing access to the confidential information.

10. The method of claim 1, further comprising notifying the individual that access to the confidential information has been provided to the requestor.

11. The method of claim 1, further comprising notifying the requestor that access to the confidential information has been provided to the requestor.

12. The method of claim 1, further comprising updating, by the first computer, the confidential information of the individual to record that access was provided to the requestor.

13. The method of claim 2, wherein information from the requester is used to determine which information is obtained from the second and third computers.

14. A method for providing emergency access, to an unregistered requestor, to personal information of a registered individual without access consent from the registered individual, the requestor being other than the individual, comprising:

receiving, at a computer from the unregistered requestor, a personal identification number associated with the registered individual, and a name of the unregistered requestor and a phone number associated with the unregistered requestor;

providing, from the computer to the requestor, a first challenge and a second challenge, the first and second challenges chosen from the set comprising: (i) whether the name of the unregistered requestor is in a first database maintained by a trusted entity, (ii) whether the name of the unregistered requestor is in a second database maintained by a governmental entity different than the trusted entity, (iii) whether a charge succeeded to a credit card number provided by the unregistered requestor, and (iv) whether a location of a device associated with the unregistered requestor was obtained;

receiving, by the computer, information responsive to the first and second challenges;

determining, by the computer, whether the received information indicates that the requestor passed the first and second challenges;

when the requestor passed the first and second challenges, providing, from the computer to the requestor, access to the personal information of the registered individual without access consent from the registered individual, a scope of access provided to the requestor for the personal information depending on which of the challenges were passed; and sending, from the computer to a contact for the registered individual, the name and phone number of the requestor;

whereby the personal information of the registered individual is available without the access consent of the registered individual only after the requestor has passed the first and second challenges from the computer.

15. The method of claim 1, further comprising obtaining the approval of the person having the specified credential, for the requestor to access the confidential information, by checking, by the first computer, a record associated with the requestor for a pre-approval indication.

16. The method of claim 1, further comprising obtaining the approval of the person having the specified credential, for the requestor to access the confidential information, by sending, from the first computer, a request for approval to a credentialed person identified in a record associated with the requestor, and receiving, at the first computer, an approval response from the credentialed person.

17. The method of claim 1, further comprising obtaining the approval of the person having the specified credential, for the requestor to access the confidential information, by
- receiving, at the first computer, contact information for a credentialed person from the requestor,
- sending, from the first computer, a request for approval to the contact information for the credentialed person, and
- receiving, at the first computer, an approval response from the credentialed person.

18. The method of claim 17, further comprising authenticating, by the first computer, the credentialed person prior to sending the request for approval.

\* \* \* \* \*